United States Patent

Holliday et al.

[11] 4,066,682
[45] Jan. 3, 1978

[54] TRANSESTERIFICATION OF BORATE ESTERS FOR PRODUCING SECONDARY ALCOHOLS

[75] Inventors: Leland Robert Holliday; Ronald Laurence Poe, both of Ponca City, Okla.

[73] Assignee: Continental Oil Company, Ponca City, Okla.

[21] Appl. No.: 702,561

[22] Filed: July 6, 1976

[51] Int. Cl.² .............................................. C07F 5/04
[52] U.S. Cl. ............................ 260/462 R; 260/632 R
[58] Field of Search ....................... 260/462 R, 632 R

[56] References Cited

U.S. PATENT DOCUMENTS 2,088,935   8/1937   Vaughn ............................ 260/462 R

FOREIGN PATENT DOCUMENTS 1,423,382   11/1965   France ............................ 260/462 R
1,005,499   4/1957    Germany ......................... 260/462 R

OTHER PUBLICATIONS

Colclough et al., J. Chem. Soc. pp. 907 & 911 (1955).
Tully et al., J. Phys. Chem. 61 1578-1579 (1957).

*Primary Examiner*—Helen M. S. Sneed
*Attorney, Agent, or Firm*—Cortlan R. Schupbach, Jr.

[57] ABSTRACT

An improved method for the transesterification of secondary alcohol borate esters with methanol, the improvement comprising separating a portion of the extractive distillation column overhead as a reflux stream and returning said reflux stream to the extractive distillation column between points located at or below the point at which the borate ester feed is introduced to the column and at or above the point at which methanol is introduced to the column, thus reducing the amount of boron-containing compounds in the crude secondary alcohol product stream.

3 Claims, 1 Drawing Figure

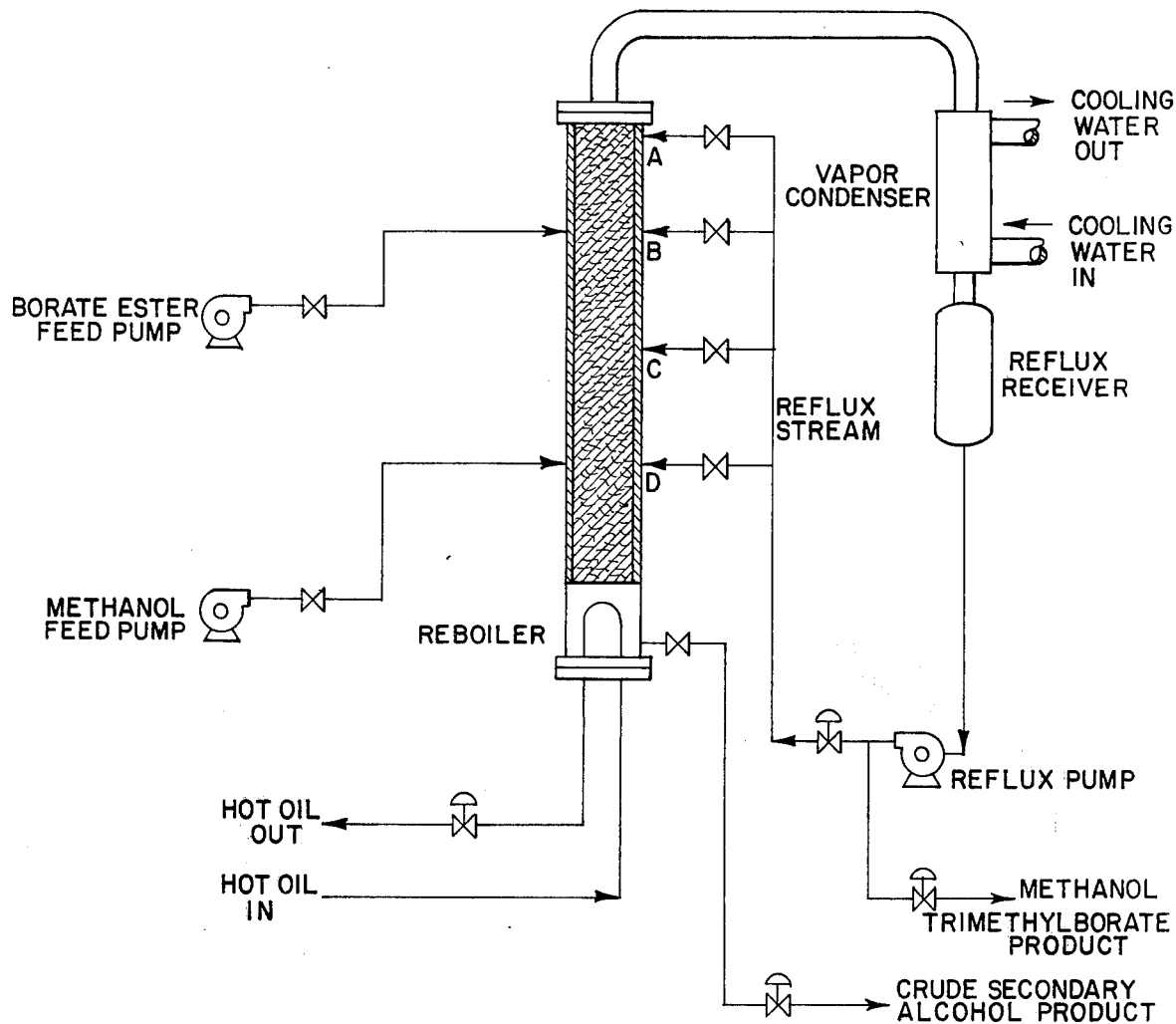

TRANSESTERIFICATION OF BORATE ESTERS FOR PRODUCING SECONDARY ALCOHOLS

This invention relates to an improved method for the transesterification of secondary alcohol borate esters with methanol. More particularly, this invention relates to an improved process which allows the reduction of boroncontaining compounds in the crude secondary alcohol product stream.

When secondary alcohols are produced by oxidizing normal paraffins in the presence of boric acid, secondary alcohol borate esters are formed. After separation of the unreacted paraffin, usually by distillation, a significant quantity of by-products remain mixed with the borate esters. The borate esters can be hydrolyzed to produce the secondary alcohols, but this process is normally not desirable since the amount of residual boron compounds remaining in the alcohol is quite high and in addition, some of the by-products enter the aqueous boric acid phase making it unsuitable for recycling without extensive purification. Thus it was clear in the art that an additional method for producing pure secondary alcohol was required.

French Pat. No. 1,423,382 discloses a process for recovering high purity boric acid which includes transesterification of secondary alcohol borate esters with methanol. The apparatus used for the transesterification is similar to an extractive distillation column, in which the boric acid ester and the methanol are fed to the column at top and bottom, respectively. The process produces crude secondary alcohols which are relatively free of boron-containing compounds and a methanol/-trimethylborate mixture from which high purity boric acid can be recovered.

However, even this process has severe disadvantages since the boron contained in the borate esters must be removed as completely as possible from the product. The previous process of transesterification has left a sufficiently high level of boron in the product stream to make the process costly and to require care in disposal. For example, boron should not be disposed around fruit-bearing trees since it is detrimental to their existence. Most product streams need to contain as little boron as possible. In addition, boron is a costly portion of the process and should be recovered as completely as possible. It is therefore clear that removal and recovery of this residual boron from the process is desirable and would be a significant advance in the art.

It is therefore an object of the present invention to provide an improved method for the transesterification of secondary alcohol borate esters with methanol which allows a reduction in the boron-containing compounds in the crude secondary alcohol product stream. Other objects will become apparent to those skilled in this art as the description proceeds.

It has now been discovered in accordance with the instant invention that the amount of boron in the crude secondary alcohol product stream can be lowered using the following procedure; in a column used for transesterifying secondary alcohol borate esters with methanol, a portion of the overhead product from the column is used as a reflux to the column. Normally, this reflux stream would be recycled to the top of the column, a conventional practice for extractive distillation and transesterification columns. In accordance with the instant invention, the reflux stream is returned to the column at a point below the top of the column. The reflux point can be varied from near the bottom of the column to near the top of the column. Preferably the reflux should be returned at a point somewhere between the middle of the column and the top. For any given column design and throughput, this invention will result in significantly lower amounts of boron-containing compounds in the recovered transesterified crude secondary alcohol.

Secondary alcohol borate esters derived from paraffin oxidation in the presence of boric acid are complex mixtures of boron compounds. The structure is theorized as described below in Equation (I). Equation (I)

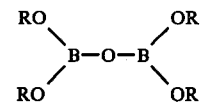

wherein R is an alkyl group having from 6 to 20 carbon atoms. However, the invention is particularly applicable to those compounds wherein R is an alkyl group having from 8 to 16 carbon atoms.

It is thought that the borate ester reacts with methanol according to the following simplified Equation (II). The equation is simplified in that the total reaction is set forth rather than the individual steps. Equation (II)

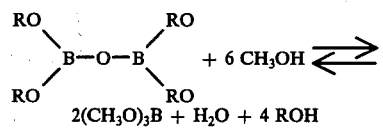

The process is normally carried out at pressures of from about 0.5 to 10 atmospheres but about 1 to 2 atmospheres are preferred. Reboiler temperatures normally range from about 250° F to about 400° F but about 350° F is preferred. Temperatures in the column normally range from about 140° F to about 180° F but about 150° F is preferred. A reflux ratio (reflux rate/distillate rate) of from about ½ to 2 is normally employed.

Experimental work using the materials described herein has shown that water is definitely formed in the reaction and can be removed from the reactor as part of the overhead product. It is believed that returning the reflux to a point between the middle and the top of the transesterification column helps to remove the water of reaction, thus obtaining maximum removal of boron from the crude secondary alcohols. It is thus theorized that the above total equation is shifted to favor alcohol formation and removal of boron compounds.

It has been unexpectedly discovered that during the transesterification, when a portion of the overhead product is used as a reflux to the column, that said reflux, instead of being inserted at the top of the column as previously carried out, should be inserted at a point at or below the borate ester feed and above the methanol feed. The reflux in the column should thus be kept between the two feed points, preferably at or below the borate ester feed point and above the methanol feed point. If the reflux is injected at or below the methanol feed or above the borate ester feed, a dramatic increase in boron content in the crude secondary alcohol product is noted.

The invention is more concretely described with reference to FIG. 1 and the examples, wherein all parts and percentages are by weight unless otherwise specified. The examples are given to illustrate the present invention and should not be construed to limit it.

FIG. 1 shows a flow diagram for a 6-inch by 10-foot continuous fractionation column used as a transesterification column in a secondary alcohol production process, generating the data for the examples below. The transesterification of secondary alcohol borate esters was carried out in the column. Point A in FIG. 1 is the top of the column, where prior art practices have sent the reflux stream. Point B is considered to be the top feed point, at the same level as the borate ester feed. Point C is the middle feed point midway between the borate ester feed and the methanol feed. Point D is the bottom feed point on the same level as the methanol feed. Each point has separate closures. The balance of the diagram is labeled to show the components used.

For all runs in the examples set forth below, the column was packed with woven stainless steel packing material and was operated at atmospheric pressure. The reboiler temperature was controlled at 350° F. Vapor was condensed and subcooled to about 70° F. The column was equipped with three feed points 2 and ½ feed apart (B, C, and D) and a conventional reflux point at the top of the column (A, at the top of the packing) while methanol was fed at the bottom feed point (Point D, 2.5 feet up from the bottom of the packing). Borate esters were fed at the top feed point (B, 2.5 feet down from the top of the packing). The reflux lines were arranged so that the reflux stream could be pumped to any of the three feed points or to the conventional reflux point. Separate runs were carried out with the results shown in Table I.

TABLE I

| Ex. | FEED RATES GALLONS PER HOUR | | Reflux Point | Reflux Rate Gallons per Hour | Crude Alcohol Boron Content ppm |
|---|---|---|---|---|---|
| | Borate Ester | Methanol | | | |
| 1 | 3 | 6 | Middle (C) | 6 | 160 |
| 2 | 3 | 6 | Top of Column (A) | 6 | 1,000 |
| 3 | 4 | 8* | Middle (C) | 8 | 620 |
| 4 | 4 | 8* | Top Feed (B) | 10 | 400 |

*Recycled methanol used, containing some trimethylborate.

Further experiments were carried out to provide comparative data for transesterification runs. The results are set forth in Table II below.

TABLE II

| Ex. | FLOW RATES, GPH | | | Reflux Point | Boron In Alcohol ppm | Methanol Feed |
|---|---|---|---|---|---|---|
| | Borate Ester | MeOH | Reflux | | | |
| 5 | 3 | 6 | 6 | A | 1,000 | Fresh |
| 6 | 3 | 6 | 6 | A | 3,000 | Fresh |
| 7 | 4 | 8 | 10 | A | 1,200 | Recycle* |
| 8 | 3 | 6 | 6 | C | 160 | Fresh |
| 9 | 4 | 6 | 6 | C | 270 | Fresh |
| 10 | 4 | 8 | 8 | C | 620 | Recycle* |
| 11 | 4 | 8 | 10 | C | 650 | Recycle* |
| 12 | 4 | 8 | 10 | B | 360 | Recycle* |
| 13 | 4 | 8 | 10 | B | 400 | Recycle* |
| 14 | 4 | 8 | 10 | D | 1,400 | Recycle* |
| 15 | 4 | 8 | 10 | D | 1,800 | Recycle* |

*Contains some trimethylborate.

Thus as the data shows, the use of a reflux stream injected into a transesterification column, according to the present invention, to produce secondary alcohols, will produce a product stream much lower in boron compounds, which allows a great savings in cost and a larger recovery of the expensive boron while reducing disposal problems. The invention is simple and is all the more surprising for its simplicity. The efficiency of the prior art process has been greatly improved by a simple rearrangement of the reflux stream although no advantage from such rearrangement was apparent.

The point at which the reflux will be reintroduced into the transesterification column will of course vary depending upon the particular characteristics of the column itself. However, in general terms, the reflux should be introduced to the column no higher than the point at which the borate ester is fed to the column and at a point no lower than the point at which the methanol is fed to the column. The ideal solution will likely lie between these points for any given column.

While certain embodiments and details have been shown for the purpose of illustrating this invention, it will be apparent to those skilled in this art that various changes and modification may be made herein without departing from the spirit or scope of the invention.

We claim:

1. An improved method for the transesterification of secondary alcohol borate esters containing alkyl groups having from about 6 to about 20 carbon atoms with methanol wherein borate esters and methanol are reacted in a transesterification column and a portion of the extractive distillation column overhead is separated and returned to the column as a reflux stream, the improvement comprising returning said reflux stream to the extractive distillation column at a point at or below the borate ester feed and above the methanol feed.

2. A process as described in claim 1 wherein the process is carried out at pressures of from about 0.5 to about 10 atmospheres.

3. A method as described in claim 1 wherein the transesterification is carried out at temperatures of from about 250° F to about 400° F.

* * * * *